United States Patent [19]

Welch et al.

[11] Patent Number: 4,855,313

[45] Date of Patent: Aug. 8, 1989

[54] METHOD OF STIMULATING CASHMERE GROWTH ON CASHMERE-PRODUCING GOATS USING MELATONIN

[76] Inventors: Robert A. S. Welch, 19 Washington Ave., Wellington; Keith Betteridge, 72 Pahiatua St., Palmerston, both of New Zealand

[21] Appl. No.: 273,185

[22] Filed: Nov. 15, 1988

Related U.S. Application Data

[63] Continuation of Ser. No. 36,397, Apr. 9, 1987, abandoned.

[30] Foreign Application Priority Data

Apr. 9, 1986 [NZ] New Zealand .................. 215767

[51] Int. Cl.$^4$ .................. A61K 31/40; A01K 6/00
[52] U.S. Cl. .................. 514/415; 424/422; 424/423; 424/438; 424/457; 424/95; 424/105; 514/962; 514/963; 514/964
[58] Field of Search .............. 424/95, 105, 422, 423, 424/438, 457; 514/415, 962, 963, 964

[56] References Cited

FOREIGN PATENT DOCUMENTS 554142 8/1986 Australia .

OTHER PUBLICATIONS

Rose et al., "Induction of Winter Fur Growth In Mink (Mustela Vison) With Melaton," 1984, J. Animal Sc, vol. 58(1), 57–61.

Chemineau et al., "Induction and Persistence of Pituitary and Ovarian Activity in the Out-of-Season Lactating Dairy Coat After a Treatment Combining a Skeleton Photoperiod, Melatonin and the Male Effect", 1986, J. Reprod. Fertil., 78(2), 497–504, CA106(3):13383j Eda, Takashi, "Hair Tonics Containing Melatonin", CA106(4):23086d.

Seamark et al., "Veterinary Implants" CA104(14):116088e.

Ellis, "Early Furring, Testicular Development and Cytotoxic Lesions of Testes and Epididymides of Dark Mink by Melatonin Implants", Adv. Biosci. 1985, 53 CA104(5):29243h.

Soversh Porod Shuachnykk Povyah Ikh Prod. 1983 64–7 (Russia) Edited by Glukhov V. F. (Chemical Abstracts vol. 102).

Photoperiodism and reproduction, Nouzilly (France), 24–25 1981.

Primary Examiner—Morton Foelak
Assistant Examiner—S. A. Acquah
Attorney, Agent, or Firm—Fleit, Jacobson, Cohn, Price, Holman & Stern

[57] ABSTRACT

The invention is a method of stimulating cashmere growth on cashmere-producing goats. The method includes administering melatonin by a sustained release delivery system.

19 Claims, No Drawings

METHOD OF STIMULATING CASHMERE GROWTH ON CASHMERE-PRODUCING GOATS USING MELATONIN

This is a continuation of application Ser. No. 36,397, filed Apr. 9, 1987, now abandoned.

This invention relates to a method for increasing the production of goat fibre. More particularly, this invention relates to a method for stimulating the growth of fibre on goats and/or controlling the goat fibre production cycle.

Three grades of goat fibre are produced by goats in New Zealand. Cashmere (<19 microns diameter) is produced by some feral goats. Mohair (>24 microns) is produced by Angora goats. Cashgora is an intermediate fibre (19–24 microns) which is produced by cross-bred animals.

In the case of a cashmere-producing goat, cashmere is the fine insulating down which is produced in secondary follicles of the skin. The remainder of the goat's coat is the coarse guard hair which is produced in primary follicles of the skin, and is generally longer. Cashmere usually comprises between 15–40% (by weight) of the total fleece. Cashmere does not have the high lustre which mohair is noted for and can be spun into yarns without having to first be mixed with another fibre such as wool. Mohair, on the other hand, is usually blended with wool before spinning. Cashmere is considered to be a higher quality fibre.

Cashmere garments are sold at the very top end of the fashion market. This is because cashmere produces such a lightweight yarn with a soft, luxuriant "handle". Cashmere is used mainly for outer garments such as pullovers, cardigans and shawls, and, to a lesser extent, underclothing.

At this stage, there is no cashmere breed of goat. Instead, goats are selected solely on their ability to produce cashmere fibre. To date, cashmere weight on feral goats ranges from 0 to 400 gm per animal per year. However, the average weight of cashmere during the New Zealand growth season 1984–85 was around 50 gm/animal. There appears to be very few goats in New Zealand capable of producing more than 300 gm of cashmere.

Cashmere is grown in China, Mongolia, Afghanistan, Iran, Australia and New Zealand. An estimated 4200 tonnes were produced in the 1983–84 season, of which 6 tonnes were produced in New Zealand.

The organisation which buys sixty percent of this production currently requires 1000 tonne more cashmere/annually and foresees a demand for a further 1000 tonne/annually in the near future. This increased production will require another 20 million goats. If the per animal cashmere production could be substantially increased, this would contribute to this high demand.

In New Zealand there are currently some 250,000 cashmere-prducing goats which, during the 1984–85 growing season, produced 6 tonnes of cashmere, valued at NZ$220,000. The cashmere producers of New Zealand (CAPRONZ), have a production target for 1990 of 130 tonnes, valued at NZ$13 m. For 1995 they are aiming for 4m goats, producing 650 tonnes of cashmere valued at NZ$100 m.

To achieve this objective, many more goats and goat farmers are required and the production of each goat must be increased substantially from 50 to 200 gm/animal. Currently in New Zealand, large numbers of feral animals are being screened for high cashmere production. Bucks with cashmere weights of 250–400 gm/animal have been identified. In Australia, feral bucks with weights of 600–800 gm/animal are being used for breeding and it seems certain that similar animals will be found in New Zealand once the screening process has been running for a time. In the meantime, high producing bucks are being imported into New Zealand from Australia and semen from these animals is being distributed around New Zealand by commercial organisations.

Unlike mohair, the price paid for cashmere fibre has maintained a steady upward trend during the last 80–90 years. The lack of violent fluctuations in price has given a lot of confidence to New Zealand farmers and investors to invest in cashmere production systems. It is essential that the per animal production is rapidly increased by breeding methods or by other means, from the low level of 50 gm, to economic levels of between 150–250 gm. We believe that the methods of the present invention will contribute substantially to this objective.

Natural cashmere growth is observed mainly during the period commencing near the longest day of the year (December in New Zealand) and finishing near the shortest day of the year (June in New Zealand). Some 1–2 months after cashmere stops growing, it sheds.

Melatonin (N-acetyl-5-methoxytryptamine) is produced in the pineal gland which is located in the brain. This hormone is only produced during the hours of darkness and thus, as day length decreases when nights become longer in the winter, melatonin is produced for a longer time. Conversely, as day length increases and nights shorten in the summer, melatonin is produced for a shorter time. It appears that melatonin is the triggering hormone for the onset of cashmere growth. Decreasing duration of melatonin production in the spring with increasing day length may also be the trigger for shedding cashmere fibres from the goat's fleece. We have produced evidence to suggest a major role of melatonin in mediating these responses.

As it now seems probable that an increasing or long duration of melatonin production is responsible for the onset of cashmere growth, we propose that by supplementing endogeneous melatonin with a sustained release delivery system containing the hormone, we can increase the level of cashmere production. Furthermore, by discontinuing the administration of supplemental melatonin, we can initiate the shedding of cashmere.

The most common method of harvesting cashmere in Australia and New Zealand is by shearing. This is done in June or July (mid-winter), prior to the time when cashmere is shed.

Shearing results in the animal being without its natural protection at the time of year when environmental stress is most severe. Many New Zealand farmers have experienced moderate to severe losses of animals following winter shearing. High abortion losses have been noted following winter shearing, which result in substantial financial loss to the farmer. Others, however, have not experienced deaths following shearing. This they attribute to having the animals in very good condition at this time. Nevertheless, extra requirements on management are needed, such as having to house the animals during bad weather, having to provide supplementary feeds, and having to provide goat shelters within paddocks.

Some New Zealand farmers are presently shearing their animal 1-2 months before the cessation of cashmere growth, so the animal can then grow a short fleece prior to cashmere growth ceasing. This system, while giving the animal some protection during the cool months of the year does mean that the potential harvest of cashmere is not attained. Delaying shearing until October or November is not a viable option, because most animals will have shed their cashmere before this time.

We believe that controlling the cashmere production cycle offers farmers the best management strategy to minimise goat losses and foetal abortion following winter shearing.

In one aspect, the present invention provides a method for stimulating the growth of fibre on goats, which method comprises administering melatonin in a sustained release delivery system to goats.

The method of the invention may be used to stimulate the growth of cashmere, or cashgora by administering the melatonin in sustained release delivery systems to cashmere-producing or cashgora-producing goats, but the preferred application of the invention is to the growth of cashmere on cashmere-producing goats.

The method of the invention may be used to stimulate the growth of fibre on goats outside of the normal goat fibre growth season.

The method of the invention may also be used to stimulate the growth of fibre on goats prior to the start of the normal goat fibre growth season and on into part of or all of the normal fibre growth season.

Alternatively the method of the invention may be used to stimulate two goat fibre growth cycles every 12 months, either by allowing a period of several weeks between cycles or by providing exogenous slowly released melatonin substantially continuously for the whole 12 months.

Accordingly, a preferred aspect of the present invention comprises a method for stimulating the growth of cashmere fibre on cashmere-producing goats by administering melatonin in a sustained release delivery system to the goats prior to the start of the normal cashmere growth season and on into part or all of the normal cashmere growth season.

It is a further aspect of the present invention that the shedding of the goat fibre at the end of a nominated fibre growth period can be initiated by ceasing the administration of melatonin to the goats, for example by removal of the sustained release delivery system containing melatonin or by designing the sustained release delivery system to administer melatonin only for the nominated period.

In this further aspect, the present invention provides a method for controlling the growth of fibre on goats, which method comprises stimulating the growth of the goat fibre by administering melatonin in a sustained release delivery system to goats and subsequently initiating the shedding of the goat fibre by discontinuing the administration of melatonin at the end of a nominated fibre growth period.

When the method of the invention is used to stimulate the growth of goat fibre outside of the normal goat fibre growth season it may be preferred to initiate the shedding of the goat fibre prior to the start of the normal goat fibre growth season, or at some time during the normal fibre growth season prior to initiating a new cycle, or prior to allowing a natural cycle to take over.

Accordingly, a further preferred aspect of the present invention comprises a method for controlling the growth of cashmere fibre on cashmere-producing goats by administering melatonin in a sustained release delivery system to the goats outside of the normal cashmere growth season and subsequently discontinuing the administration of melatonin prior to the start of the normal cashmere growth season.

It will be seen from the foregoing that the method of the present invention could be used to control the cashmere production cycle (a) by stimulating out-of-season growth of cashmere so that the animals can be shorn at some time of the year other than winter, (b) by stimulating more rapid growth of cashmere than is normal, thereby enabling two shorter growth seasons per year, producing as much or more total cashmere per annum, (c) by stimulating the growth of cashmere prior to the start of the normal fibre growth season thereby lengthening the period of fibre growth in each year, (d) by stimulating more rapid growth of cashmere during the early part of the normal fibre growth season, thereby increasing the weight of cashmere shorn in a single shear in autumn or winter, and (e) by stimulating out-of-season growth of cashmere and then initiating the shedding of cashmere fibres prior to the start of a new fibre growth season.

The following Example show that melatonin will induce cashmere fibre growth out-of-season. We believe the main potential of the method of the invention to be in the sustained release administration of melatonin in the period prior to the commencement of normal growth until such time as cashmere fibres cease to grow further. We believe that, after a resting period from exogenous melatonin, a natural fibre growth cycle may commence, or a second artificially induced growth cycle may be initiated by further melatonin treatment.

A further alternative use of the invention may be to administer melatonin continuously so as to override the animal's melatonin-controlled biological rhythm of growth and thereby initiate biological rhythms independent of melatonin control.

Work with cattle in France and the United Kingdom has found that melatonin reduces appetite and thereby slows growth relative to control cattle. This has not happened with the goats in the trials reported in the following Examples.

The melatonin is preferably administered to the goats via a subcutaneous or intramuscular sustained release delivery system, for example a polymer matrix which may be implanted in or injected into the animal and from which the melatonin is released by diffusion from or erosion of the polymer matrix.

Although silicone rubber implants containing melatonin were used in the following Examples, they require surgery to insert and remove the implants and thus may not be practical for commercial applications. The formulation of injectable, slow-release, drug delivery systems containing melatonin as the active ingredient will enable large-scale administration of melatonin to commercial goat flocks. Such delivery systems are known in pharmaceutical and veterinary practice for other active ingredients. For example, we envisage the administration to goats of injectable micro-encapsulated melatonin formulations having sustained or controlled release of the melatonin being the preferred form of administration.

The sustained release delivery system and the dosage levels of melatonin therein will be chosen so as to provide a duration of melatonin release, a rate of melatonin release and a blood level of melatonin sufficient to provide the desired stimulation of goat fibre growth in the subject goats. The sustained release delivery system may be so formulated as to provide a rate of melatonin release and a blood level of melatonin sufficient to provide the desired stimulation of goat fibre growth in the subject goats but only for the duration of a nominated fibre growth period.

Blood levels of melatonin sufficient to provide stimulation of fibre growth in goats will be in excess of 100 pg/ml of melatonin in blood plasma and minimum effective blood levels may be as high as 200 pg/ml.

The method of the invention in its various aspects is illustrated in the following Examples.

EXAMPLE 1

In September 1985 we prepared silicone rubber implants containing melatonin. Each implant consisted of 3 g silicone rubber (Dow Corning Medical Grade 380) containing 150 mg melatonin. These implants were implanted under the skin of 20 goats which had been shorn in July of that year. One aim of this trial was to determine whether there were any serious side-effects of the drug on pregnant animals. 19 animals in the trial did not receive the implant, and acted as controls. Six weeks later those animals receiving an implant had produced significant amounts of cashmere and guard hair, whereas the control animals had produced no cashmere at all. Total fibre growth was four times greater on treated animals than on control animals (1.7 v 0.4 mg/sq cm/wk respectively). Fibre diameters confirmed that the extra growth was both cashmere and guard hair (16.2% cashmere by/weight) where, by contrast, the minimal growth on the control animals was wholly guard hair (i.e. 0% cashmere by weight). Only 9 of the 20 animals retained their implants for the duration of the initial 6-week phase of the trial. Five weeks later, 5 of these implants were still intact. These were replaced with new implants to ensure a continued high level of melatonin in the bloodstream. These animals were maintained under trial conditions for a further $6\frac{1}{2}$ weeks. In mid-January 1986, all animals were shorn and fleeces weighed. The 5 retreated goats, which had been treated for up to $17\frac{1}{2}$ weeks, grew substantially more total fibre in the period from July 1985 than either those goats which had been treated for up to 11 weeks or the untreated control animals (157 v 98 v 69 g respectively). For the retreated animals this growth represented 66% of the total fleece shorn in July 1985 and the cashmere was 19% by weight of the January fleece. Subsequent to the removal of the melatonin implants, cashmere produced while the implants were in place was shed although new cashmere continued to grow, presumably due to stimulation from endogenous melatonin. Those treated animals which lost their implants and were not retreated only had 2% by weight of cashmere in their fleeces shorn in January. This was because removal of exogenous melatonin had caused September/October-grown cashmere fibres to shed before the January shearing.

To summarise this Example:

1. Melatonin induced substantial out-of-season cashmere growth.

2. This advantage was still apparent following January shearing, even though some control animals had been growing cashmere since December.

3. Liveweight gain of implanted animals was no different from that of control animals.

4. There were no apparent adverse effects on pregnant animals, on kids from implanted animals or on general health of treated animals.

5. Cashmere was shed following the removal of melatonin implants in January.

6. Cashmere stimulated to grow in September/October was shed prior to January shearing from goats which lost their implants during September and October.

EXAMPLE 2

In December 1985 we implanted melatonin implants, as described in Example 1, into 10 non-lactating, non-pregnant 15 month old does and 10 similar does of mixed ages. 10 similarly aged does were not treated. Implants remained in place for $6\frac{1}{2}$ weeks. The aim of the trial was to see if cashmere fibre could be stimulated to grow in the late out-of-season period and the early 'normal growth' period. Fibre growth measured on midside patches was similar on young and old goats and on treated and untreated goats. However, cashmere weight was 100% greater in the melatonin treated goats due to the higher cashmere content of the fleece (1.8 v 0.9 mg/sq cm/ wk respectively); ($P<0.005$). Melatonin had no effect on liveweight gain of these non-lactating, non-pregnant does compared to the untreated does.

To summarise this Example:

1. Melatonin induced a faster rate of growth of cashmere fibre in both young and older goats.

2. The cashmere content of the fleece was greater in treated goats although total fibre growth was similar between treated and untreated goats.

3. Liveweight gain of treated does was similar to that of control does.

EXAMPLE 3

In March 1986 ten 18 month does and ten mixed-age does were treated with a single melatonin implant as described in Example 1. Twenty does remained untreated. The objective of this 6 week trial was to further study the effect of melatonin on liveweight changes and on growth of goat fibre during the normal fibre growing season. Melatonin had no effect on liveweight gain of these non-lactating does compared to the untreated goats.

Total goat fibre growth during the 6 week trial was greater on untreated goats. However, treated goats had a higher percentage by weight of cashmere in the fleece than untreated goats (51% v 41%) ($P<0.05$) with the result that cashmere weights were similar in each group (1.3 and 1.4 mg/sq cm/ wk) for melatonin and untreated goats respectively.

To summarise this Example:

1. Melatonin treatment had no effect on liveweight gain of does.

2. The percentage cashmere content in the regrown fibre was increased by melatonin treatment.

3. Weight of cashmere in the 6 week regrowth was not increased by use of melatonin.

EXAMPLE 4

In September 1986 35 feral wether goats of mixed age were divided into groups: untreated (7); $\frac{1}{4}$ implant (5); $\frac{1}{2}$ implant (5); 1 implant (5); 2 implants (5); microcapsule formulation I (M.C.I.) (5); microcapsule formulation II (M.C.II) (3). The implants were made and implanted as described in Example 1 except that ¼ and ½ implants were single implants cut to ¼ and ½ length to effect a reduced dosage. The microcapsules were made according to a formulation of Stolle Research & Development Corporation, Ohio, USA, and contained malatonin at a level believed to equate with the daily release characteristics of a single implant. The microcapsules were suspended in physiological saline containing 2% (w/w) carboxymethyl cellulose immediately prior to injection. Two millilitres (total volume) was injected intramuscularly into each animal.

The objects of this trial were:

(a) to repeat the stimulation of out-of-season growth of cashmere as obtained in Example 1, (b) to determine whether there was a dose response characteristic between daily melatonin concentration in the serum of goats and the amount of cashmere fibre stimulated to grow out-of-season, and (c) to characterise the pattern and rate of melatonin release from two microcapsule formulations. Serum samples were obtained before, during and after the administration of melatonin in the implant form. Implants were removed after the 6 week trial duration. Micocapsules were administered at the same time as implants but could not be removed after the 6 week trial duration. Fibre growth was measured from shaved patches on the midside of each goat. Serum melatonin levels two weeks after implantation and cashmere fibre responses were:

|  | pg/ml serum (+/−SE) | | mg cashmere/sq cm/6 wk (+/−SE) | |
|---|---|---|---|---|
| untreated | 6.0 | (0.5) | 0 | (0.0) |
| ¼ implant | 100.1 | (31.6) | 1.51 | (0.87) |
| ½ | 65.3 | (4.1) | 1.32 | (0.80) |
| 1 | 329.0 | (93.3) | 1.86 | (0.77)* |
| 2 | 437.0 | (78.1) | 1.68 | (0.86)* |
| M.C.I. | 358.5 | (38.2) | 2.71 | (0.89)* |
| M.C.II | 393.6 | (49.4) | 3.11 | (0.87)* |

*(P < 0.05) significantly increased over untreated goats.

These results may indicate a dose response or a requirement to maintain a blood level of melatonin above a threshold level, but closer definition of this will be required with larger group sizes.

One month after implants were removed the goats were again sampled for fibre growth. All previously treated goats had grown significantly more total fibre and cashmere than untreated goats. During the next four week period of fibre growth, that is 4–8 weeks after implant removal, and into the normal fibre growth season, untreated goats had grown more fibre than previously-treated goats. Removal of implants, and degradation of microcapsules induced shedding of cashmere.

EXAMPLE 5

In November 1986 16 mixed aged first cross (Angora×feral) wethers were divided into two groups. One group received a melatonin implant as described in Example 1 and the others were untreated. Fibre regrowth from patches on the midside of each goat was measured after ten weeks. The objective of this trial was to determine whether cross-bred goats grew more cashgora (a coarser down than cashmere) when given melatonin. Treated goats appered to grow more total fleece (4.5 and 4.0 mg/sq cm/wk for treated and untreated goats respectively) and more down (3.4 and 2.6 mg/sq cm/ week for treated and untreated goats respectively) but these effects were not statistically significant (P>0.05). This may possibly have been due to the small sample size; and that November-January was close to or within the normal fibre growing period for these animals.

EXAMPLE 6

In May 1986 we implanted melatonin implants, as described in Example 1, into 20 does of mixed age. A further 20 animals were used as untreated controls. In June, July and August further groups of 20 does were given melatonin implants. Implants were replaced every 2 months to ensure the maintenance of high blood melatonin concentrations. Untreated control animals and those animals first implanted in May and August have been maintained to the present date (April 1987). The groups first implanted in June and July were discontinued in November. The aim of the trial was to see if the natural cashmere growing cycle could be extended and shedding delayed. Up till March 1987, the treated goats had not produced significantly more cashmere than control animals. Shedding of the cashmere was not delayed in the treated animals as compared with the control animals.

What we claim is:

1. A method for stimulating the growth of cashmere fibre on cashmere-producing goats, which method comprises administering melatonin in a sustained release delivery system to the goats.

2. A method according to claim 1, which comprises administering melatonin in a sustained release delivery system to cashmere-producing goats outside of the normal cashmere growth season.

3. A method according to claim 1, which comprises administering melatonin in a sustained release delivery system to cashmere-producing goats prior to the start of the normal cashmere growth season and on into part of or all of the normal cashmere growth season.

4. A method according to claim 1, which comprises administering melatonin in a sustained release delivery system to cashmere-producing goats during the early part of the normal cashmere growth season.

5. A method according to claim 1, which comprises administering melatonin in a sustained release delivery system to cashmere-producing goats both outside of the normal cashmere growth season and during the normal cashmere growth season, allowing a period of several weeks between each period of administration.

6. A method according to claim 1, which comprises administering melatonin in a sustained release delivery system to cashmere-producing goals substantially continuously throughout the year.

7. A method for stimulating the growth of cashmere fibre on cashmere-producing goats which comprises administering melatonin in a sustained release delivery system to the goats prior to the start of the normal cashmere growth season and on into part or all of the normal cashmere growth season.

8. A method for controlling the growth of cashmere fibre on cashmere-producing goats, which method comprises stimulating the growth of the cashmere by administering melatonin in a sustained release delivery system to the goats and subsequently initiating the shedding of the cashmere by discontinuing the administration of melatonin at the end of a nominated cashmere growth period.

9. A method according to claim 8, which comprises administering melatonin in a sustained release delivery system to cashmere-producing goats outside of the normal cashmere growth season and discontinuing the administration of melatonin prior to the start of the normal cashmere growth season.

10. A method according to claim 8, which comprises administering melatonin in a sustained release delivery system to cashmere-producing goats prior to the start of the normal cashmere growth season and on into part of the normal cashmere growth season and discontinuing the administration of melatonin during the normal cashmere growth season.

11. A method for controlling the growth of cashmere fibre on cashmere-producing goats by administering melatonin in a sustained release delivery system to the goats outside of the normal cashmere growth season and subsequently discontinuing the administration of melatonin prior to the start of the normal cashmere growth season.

12. A method according to claim 1, wherein the melatonin is administered in a sustained release delivery system consisting of an implant.

13. A method according to claim 1, wherein melatonin is administered in a sustained release delivery system consisting of an injectable microcapsule formulation.

14. A method according to claim 1, wherein in melatonin is administered in a sustained release delivery system consisting of an implant.

15. A method according to claim 7, wherein the melatonin is administered in a sustained release delivery system consisting of an implant.

16. A method according to claim 10, wherein the melatonin is administered in a sustained release delivery system consisting of an implant.

17. A method according to claim 8, wherein melatonin is administered in a sustained release delivery system consisting of an injectable microcapsule formulation.

18. A method according to claim 7, wherein melatonin is administered in a sustained release delivery system consisting of an injectable microcapsule formulation.

19. A method according to claim 10, wherein melatonin is administered in a sustained release delivery system consisting of an injectable microcapsule formulation.

* * * * *